United States Patent [19]

Abramsky et al.

[11] Patent Number: 5,580,882
[45] Date of Patent: Dec. 3, 1996

[54] USE OF SUBSTITUTED QUINOLINE CARBOXAMIDE

[75] Inventors: Oded Abramsky; Dimitrios Karussis, both of Jerusalem; Dan Lehamann, Yearim; Shimon Slavin, Jerusalem, all of Israel

[73] Assignee: Kabi Pharmacia AB, Helsingborg, Sweden

[21] Appl. No.: 211,579

[22] PCT Filed: Oct. 8, 1992

[86] PCT No.: PCT/SE92/00705

§ 371 Date: Apr. 8, 1994

§ 102(e) Date: Apr. 8, 1994

[87] PCT Pub. No.: WO93/06829

PCT Pub. Date: Apr. 15, 1993

[30] Foreign Application Priority Data

Oct. 9, 1991 [SE] Sweden .................................. 9102909

[51] Int. Cl.[6] .................................................. A61K 31/47
[52] U.S. Cl. ............................................................. 514/312
[58] Field of Search ................................................ 514/312

[56] References Cited

U.S. PATENT DOCUMENTS 4,547,511 10/1985 Eriksoo et al. ........................ 514/312
5,310,913 5/1994 Gunnarsson et al. .................. 514/312

OTHER PUBLICATIONS

Carlsten, H., *APMIS*, 97:728, 1989.
Cook, S. D., *Ann. Neurol.* 22:634–638, 1987.
Dhib–Jalbut, S., *Annal. Allergy*, 64:433–444, 1990.
Hauser, S. L., *N. Eng. J. Med.*, 308:173–183, 1983.
Kalland, T., *J. Immunol.*, 134:3956, 1985.
Kalland, T., *Cancer Res.*, 46:3018, 1986.
Kalland, T., *J. Immunol.*, 144:4472–4476, 1990.
Kappos, L., *Ann. Neurol.*, 23:56–63, 1988.
Karussis, D. M., *Autoimmunity* 1992:101.
Karussis, D. M., *J. Neurol.*, 1992, 239 (suppl 2):S96.
Karussis, D. M., *Neurology* 42 (suppl 3):346, 1990.
Karussis, D. M., *J. Neuroimmunol.*, 1991; 1(suppl):159.
Larsson, E. L., *Int. J. Immunopharmacol.*, 9:425, 1987.
Mehta, P. J., *Neurol.*, 32:372–77, 1982.
Myrianthopoulos, N. C., *Handbook of Clinical Neurology*, 47:289, 1985.
Oksenberg, J. R., *Nature*, 345:344–347, 1990.
Patzold, U., *J. Neurolog. Sci.*, 54:377–394, 1982.
Prineas, J. W., Koetsier, J. C. (ed.) Handbook of Clinical Neurology, pp. 213–257, Elsevier Science Publ., Amsterdam, 1985.
Tarkowski, A., *Arthr. Rheum.*, 29:1405–1409, 1986.

*Primary Examiner*—Jerome D. Goldberg
*Attorney, Agent, or Firm*—Pravel, Hewitt, Kimball & Krieger

[57] ABSTRACT

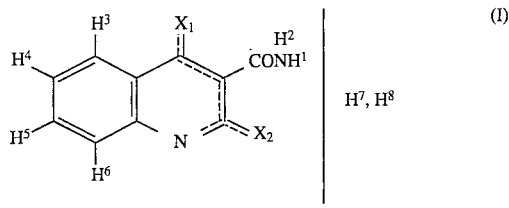

The use of an anti-MS quinoline-3-carboxamide compound comprising the structure of formula (I), optionally with substituents for the $H^{1-9}$ hydrogen, or a salt of said compound where (a) ------------ represents that there are two conjugated double bonds between atoms comprised by the dashed line (only formula I), (b) the hydrogens $H^7$ and $H^8$ are attached to different atoms selected from $X_1$, $X_2$ and the nitrogen atom in the quinoline ring, (c) $X_1$ and $X_2$ are independently selected from an oxygen atom or an $NH^9$ group, said $X_1$ and $X_2$ being bound by a single bond to the ring when carrying $H_7$ or $H_8$ and by a double bond when not carrying $H^7$ or $H^8$, for the manufacture of a composition intended for the treatment of conditions associated with MS. Also described are treatment regimens for MS patients. The particularly preferred compound is roquinimex or a salt thereof.

2 Claims, 2 Drawing Sheets

USE OF SUBSTITUTED QUINOLINE CARBOXAMIDE

The present invention concerns the use of Quinoline-3carboxamide compounds, in particular roquinimex (Linomide®), or a pharmaceutically and physiologically acceptable salt thereof that is therapeutically active, for the treatment of multiple sclerosis (MS).

BACKGROUND OF THE INVENTION

Multiple sclerosis (MS) is the most common acquired neurologic disease of young adults in we, stem Europe and North America. It accounts for more disability and financial loss, both in lost income and in medical care, than any other neurologic disease of this age group. There are approximately 250.000 cases of MS in the United States.

MS affects the central nervous system and involves a demyelination process i.e. the myelin sheats are lost whereas the axons are preserved. In the central nervous system (CNS), oligodendrocytes send out processes to axons that envelope them with layers of plasma membrane that are compacted and then constitute the myelin. Myelin provides the isolating material that enables rapid nerve impulse conduction. Evidently, in demyelination, this property is lost. Although the pathogenic mechanisms responsible for MS are not understood, several lines of evidence indicate that demyelination has an immunopathologic basis. The pathologic lesions, the plaques, are characterized by infiltration of immunologically active cells such as plasma cells, macrophages and activated T cells (1). The T cells present in the cerebrospinal fluid of MS patients during acute attacks have been reported to be oligoclonal as judged by their T cell receptor usage, a finding which indicate a response to a particular antigen (2). The latter suggestion is also supported by immunogenetic studies showing an association of MS with certain MHC class II alleles (3). Increased cerebrospinal fluid immunoglobulin is consistently found in MS (4), and a variety of abnormalities in T cell functions have been described (5).

The ultimate treatment of MS would be the repair of damaged CNS myelin. Although there is no indication that the goal will be achieved soon, recent advances in understanding the biology of glial cells (which manufacture and maintain myelin) suggest that such treatment may be feasible eventually. Current treatment of MS falls into three categories: treatment of acute exacerbations, modulation of progressive disease, and therapy for specific symptoms.

Corticosteroids and ACTH have been shown to be useful in shortening the mount of time required for recovery from an exacerbation of MS. The mechanism of this effect is unknown. These medications do not increase the extent of recovery, nor do they prevent subsequent exacerbations. It has been established recently that corticosteroids are as useful as ACTH for treatment of acute exacerbations. Neither medication has been shown to be beneficial in chronic administration. Use of corticosteroids should be reserved for the treatment of dear-cut neurologic signs that are disabling. For the treatment of life-threatening exacerbations, most commonly, involving brain stem compromise, methylprednisolone in large doses (1 g IV daily for three days) has been used.

Hyperbaric oxygen treatment has recently been shown in several well-controlled trials to be completely ineffective as a treatment for all forms of MS. The antiviral substance transfer factor has been shown to be ineffective in a limited trial.

Since the immune system is believed to be involved in the development of the pathogenic process in MS, the use of immunosuppressive therapy has recently received widespread attention. Cyclophosphamide, administered in a regimen sufficient to induce lymphopenia, has been demonstrated to stabilize symptoms in patients with chronic progressive MS. Unfortunately, the effect is transient and treated and control patients are indistinguishable 3 years after treatment (6). Other general immunosuppressive treatment such as total lymphoid irradiation or treatment with azathioprine has only resulted in slight effects on symptoms (7, 8). Recently, a large multicenter trial of cyclosporine A indicates that this treatment slows the profession of the disease (9). More specific immunosuppressive treatment of MS is currently being evaluated in clinical trials and include monoclonal antibodies to T cell populations, vaccination against T cells or low dose heparin to prevent migration of T cells into the central nervous system (5). A common denominator of all these treatment regimen is that they are immunosuppressive and the rationale of their use is to suppress immune reactivity against nervous-tissue.

Quinoline-3-carboxamide compounds have been suggested as pharmaceuticals in the prior art. These compounds comprise the structure given in formula I below, optionally with substituents for the hydrogens $H^{1-9}$, and where appropriate, pharmaceutically and physiologically acceptable and therapeutically active salts of the compounds.

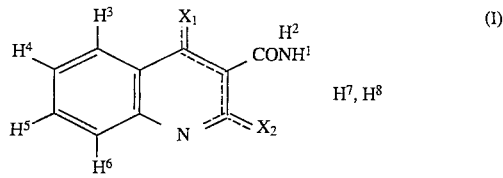

Formula I is a collective formula for the tautomeric structures II–IV.

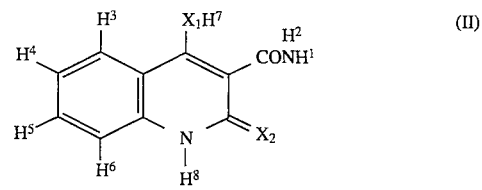

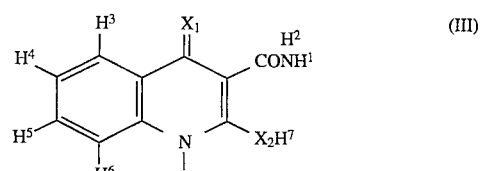

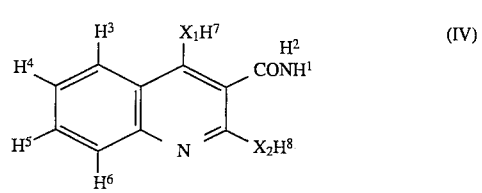

In these formulae (a) ------------ represents that there are two conjugated double bonds between atoms comprised by the dashed line (only formula I).

(b) The hydrogens $H^7$ and $H^8$ are attached to different atoms selected from $X_1$, $X_2$ and the nitrogen atom in the quinoline ring (c) $X_1$ and $X_2$ are independently selected from an oxygen atom or an $NH^9$ group, said $X_1$ and $X_2$ being bound by a single bond to the ring when carrying $H^7$ or $H^8$ and by a double bond when not carrying $H^7$ or $H^8$.

The substituents that, according to the prior art, my replace $H^{1-9}$ can in principle be any substituent that gives compounds that can be isolated. See for instance Indian journal of Chemistry Vol 17B (1979) 488–90 (and-inflammatory properties), U.S. Pat. No. 3,960,868 (=GB 1,467,061, analgesic, anticonceptive, anti-inflammatory and anti-allergic properties), U.S. Pat. No. 4,547,511 and U.S. Pat. No. 4,738,971 (enhancing cell-mediated immunity), WO 9015052 (U.S. Ser. No. 651,234, filed May 31, 1990, immune modulator), U.S. Pat. No. 4,107,310 (analgetics) and JP 68023948 (bacteriocides). US patents and patent applications given above are hereby imcorporated by reference. In general it can be stated that many of the compounds comprised by formula I are classified as immune modulators with individual effects spanning the spectra from suppression to stimulation of the immune system. The specific effect achieved depends on the substituents.

Among the compounds of formula I, N-phenyl-N-methyl-1,2-dihydro-4-hydroxy-1-methyl-2-oxo-quinoline -3-carboxamide Linomide®, LS 2616 with the generic name roquinimex) and its salts as defined above have ,for the time being appeared the most promising drug candidate i.e. a compound of structure II with a phenyl substituent for $H^1$, a methyl substituent for each of $H^2$ and $H^8$ ($H^8$ being attached to the nitrogen atom of the quinoline ring), with no substituents for $H^{3-7}$ and $H^7$ attached to $X_1$, and each of $X_1$ and $X_2$ being an oxygen atom. The compound has double bonds between positions 3 and 4 and between positions 2 and $X_2$ positions refer to those of the quinoline ring).

The scientific experimentation with roquinimex has shown that the compound has multiple immunological activities. It has thus been found that roquinimex increases the proliferative response to T and B cell mitogens (10), enhances antibody production (11) and augments NK cell activity (12). Moreover, its immunostimulating properties may be useful in the treatment of tumours (14), and systemic lupus erythematosus (15) as suggested in U.S. Pat. Nos. 4,547,511 and 4,738,971. During the priority year our results with roquinimex (Linomide®) have been published (16–19).

OBJECTIVES OF THE INVENTION

Figure 1:
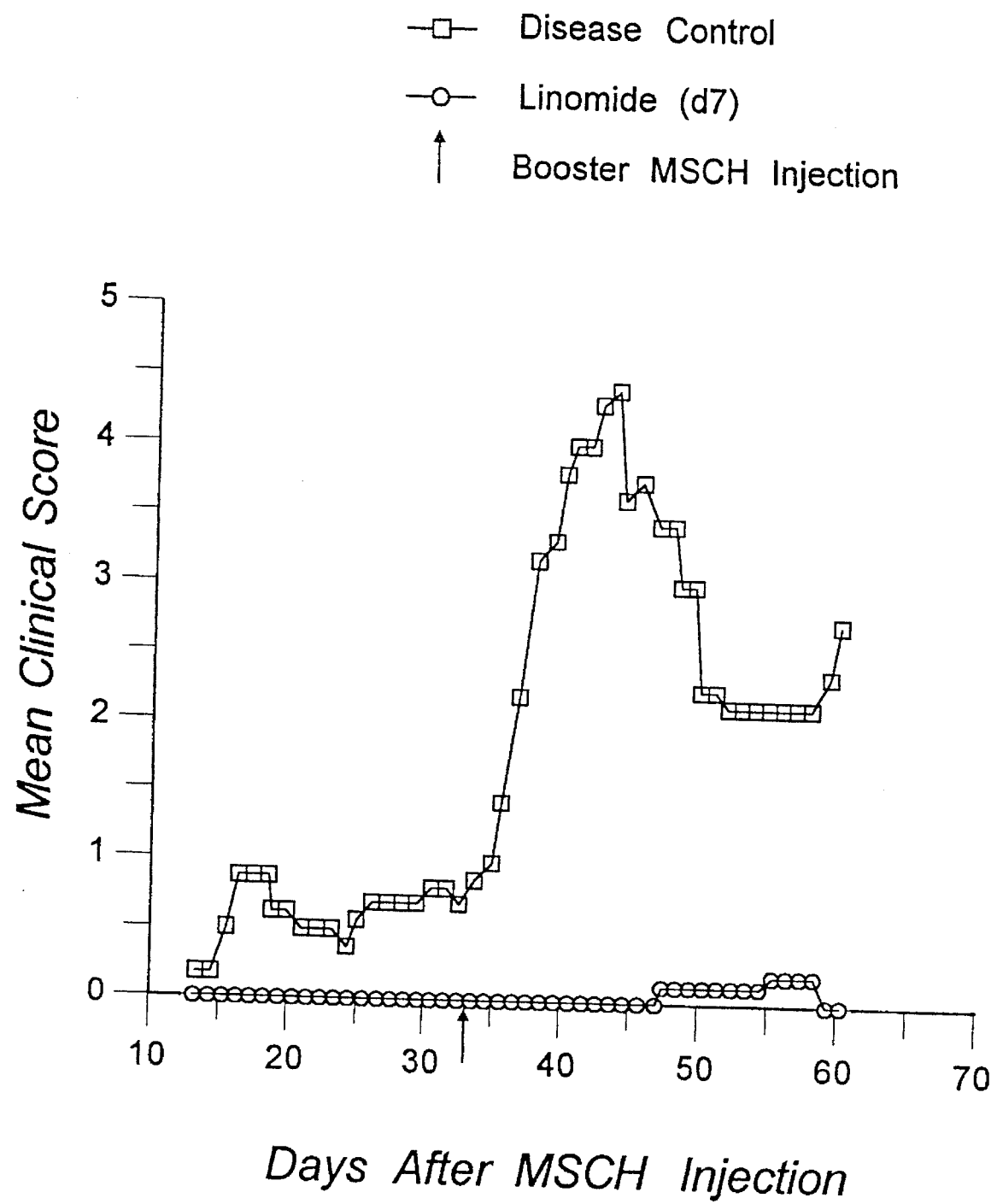
FIG. 1 is a graph showing mean clinical score of signs of chronic-relapsing experimental autoimmune encephalo-myelitis (CR-EAE) as a function of time after induction of disease in animals by injection of mouse spinal cord homogenate (MSCH). Squares represent untreated, diseased controls. Circles represent diseased animals treated daily with linomide (d7), beginning on day seven post MSCH injection.

One major objective of the invention is to provide a method for treatment of multiple sclerosis and its manifestations, such as paralytic attacks with periods of remissions, demyelinating lesions of the white matter and lymphocytic infiltrations into the brain and spinal cord.

A second major objective is to provide drugs to be used for the manufacture of pharmaceutical compositions intended for the treatment of the conditions given in the preceding paragraph.

In the invention mammalian species that can develop multiple sclerosis are treated, e.g. humans.

THE INVENTION

Based on our study of the pronounced immune stimulator roquinimex in the CR-EAE model in SJL/mice (see below), we have found that in contrast to earlier treatment strategies based on immunosuppression roquinimex exerts an extremely efficient anti-EAE/MS effect. By studying other quinoline-3-carboxamide compounds comprising the structure given in formula I in the same model as outlined in the experimental part, further drug candidates showing similar effects will be found.

Thus the present invention concerns a method for the treatment of multiple sclerosis and its clinical and pathological manifestations. The method means administration of a therapeutically effective amount of an anti-MS compound comprising the structure given in formula 1. The inventive method includes prophylactic treatment i.e. administration of the anti-MS compound before the onset of clinical signs. The invention also comprises the use of the compounds for the manufacture of a pharmaceutical composition to be employed in the method.

For the time being it is believed that the most preferred compounds can be found among those described in U.S. Pat. Nos. 4,738,971 and 4,547,511. In particular combinations of substituents may be selected from:

(i) $H^8$ is replaced by a group selected from lower alkyls ($C_{1-8}$) that are bound to the nitrogen atom of the quinoline ring ($H^8$=lower alkyl).

(ii) $X_1$ is an oxygen atom to which $H^7$ is bound ($X_1$=—OH group).

(iii) $X_2$ is oxygen which is linked to the quinoline ring by a double bond).

(iv) $H^1$ is replaced by an aryl, in particular a phenyl group ($H^1$=aryl, in particular a phenyl group ($H^1$=aryl, in particular phenyl) and/or $H^2$ by a lower alkyl ($C_{1-8}$).

The compounds may be used in the form of salts as defined above, e.g. a Na- or Ca-salt. Particularly preferred is Roquinimex and its salts as given above.

By the term effective mount is meant that the mount shall ameliorate the MS manifestations/effects discussed above.

The administration route is primarily oral, but this does not exclude other routes, such as parenteral, intraperitoneal, injection, infusion, rectal etc. administration.

The composition referred to by the invention may contain the active compound as such or, where appropriate, in the form of a salt of a pharmaceutically and physiologically acceptable cation or anion as known in the art. A conceivable dosage range is from 0.100 mg a day, depending on the specific condition to be treated, the age and weight of the patient, and the patient's specific response to the medication. Normally the effective dosage mount is from 0.01–10, preferably 0.05–1 mg/kg body weight.

Formulations that may be used are powder, syrups, suppositories, ointments, solutions, pills, capsules, pellets etc. with or without, but preferably with, pharmaceutically acceptable carriers. See further U.S. Pat. Nos. 4,738,971 and 4,547,511 that are incorporated by reference.

EXPERIMENTAL MODEL

Chronic-relapsing experimental autoimmune encephalomyelitis (CR-EAE) of SJU/J mice is a disease of the central nervous system (CNS), characterized clinically by waves of paralytic attacks and periods of remissions and pathologically by demyelinating lesions of the white matter and lymphocytic infiltrations into the brain and spinal cord. CR-EAE has been extensively used as a model of experimental demyelination, resembling in many aspects human multiple sclerosis (MS). The disease can be induced by two subcutaneous injections of mouse Spinal cord homogenate (MSCH) emulsified in Freund's complete adjuvant.

Several immunomodulating agents have been used previously for treatment of CR-EAE (and of MS d above), including steroids, cyclophosphamide, cydosporin-A, copolymer 1 (COP-1), TLI and monoclonal antibodies, none with fully satisfactory results.

The present study was designed to evaluate the effect of Linomide on the course of CR-EAE.

MATERIALS AND METHODS

Mice: Female, 6–12 weeks old SJL/J mice were purchased from the Jackson Laboratory, Bar Harbor, Me., USA and maintained in top filtered cages and fed with add/fled water (pH:4) without antibiotics and regular diet.

Antigang: Mouse spinal cord homogenate (MSCH) was obtained from 3 to 10 month old mice (various strains) by insufflation and lyophilization at −20° C.

Linomide administration: Linomide (Kabi Pharmacia Therapeutics AB, Helsingborg, Sweden) was dissolved in drinking water in a concentration of 0,5 mg/ml. It only slightly influenced (reduced) water consumption. Each mouse received an estimated quantity of 1,5–2,5 mg/day (60–100 mg/kg). Linomide administration was initiated on day 7 or 14 post immunization for CR-EAE and discontinued 3–4 weeks later. A fresh dilution of the drug was prepared every 10 days. Control animals received regular acidified water only.

Immunization for CR-EAE: CR-EAE was induced according to Brown's immunization protocol, with slight modifications. Briefly, mice were injected subcutaneously in one site over the left flank with a mixture of 1 mg of MSCH in 0,15 ml of phosphate buffered saline (PBS) and 0,03 mg of Mycobacterium tuberculosis hominis H37Ra, in 0,15 ml of incomplete Freund's adjuvant (ICFA, Difco Laboratories, Mich.). Each mouse received a second inoculation into the contralateral Bank with the same antigen-adjuvant mixture, 7 days later. First clinical signs of disease were seen 12–14 days post immunization and a chronic disease with relapses, and remissions followed the first attack. A third injection with the same encephalitogenic inoculum produced a severe relapse 6–7 days later.

Clinical evaluation of CR-EAE: Animals were examined daily for sip of disease and graded on a 0 to 6 scale of increasing severity, as follows:

(0): no evidence of disease; (1): mild tail weakness (floppy tail); (2): tail paralysis with mild hind leg weakness; (3): hind leg paresis; (4): hind leg paralysis and mild forelimb weakness; (5): quadriplegia or moribund state; (6): death.

Histologic evaluation: For routine histology, mice were sacrificed using ether anesthesia and then perfused extensively with PBS-buffered formalin. Brains and spinal cords were removed and then processed for parafin embedding. Tissue sections were stained with hematoxylin and eosin as well as Luxol fast blue.

RESULTS

1. Linomide administration on day 7 post immunization
As shown in FIG. 1 and table 1, continuous administration of Linomide orally, starting on day 7 following immunization with the encephalitogenic antigen completely prevented clinical signs of CR-EAE in all of the 16 treated mice in two separate experiments, whereas 19/20 control mice developed chronic-relapsing paralysis. Two of the treated mice developed a very mild weakness (grade 1 ) 2–7 days after discontinuation of the drug. The rest remained free of disease for a period of more than 60 days. Booster injection of MSCH caused a severe recurrent attack with high mortality (60 %) in 10/10 of the untreated mice but left totally unaffected all 8 Linomide treated animals (FIG. 1, table 1).

2. Linomide administration on day 14 post immunization (one day after onset of disease)

Figure 2:
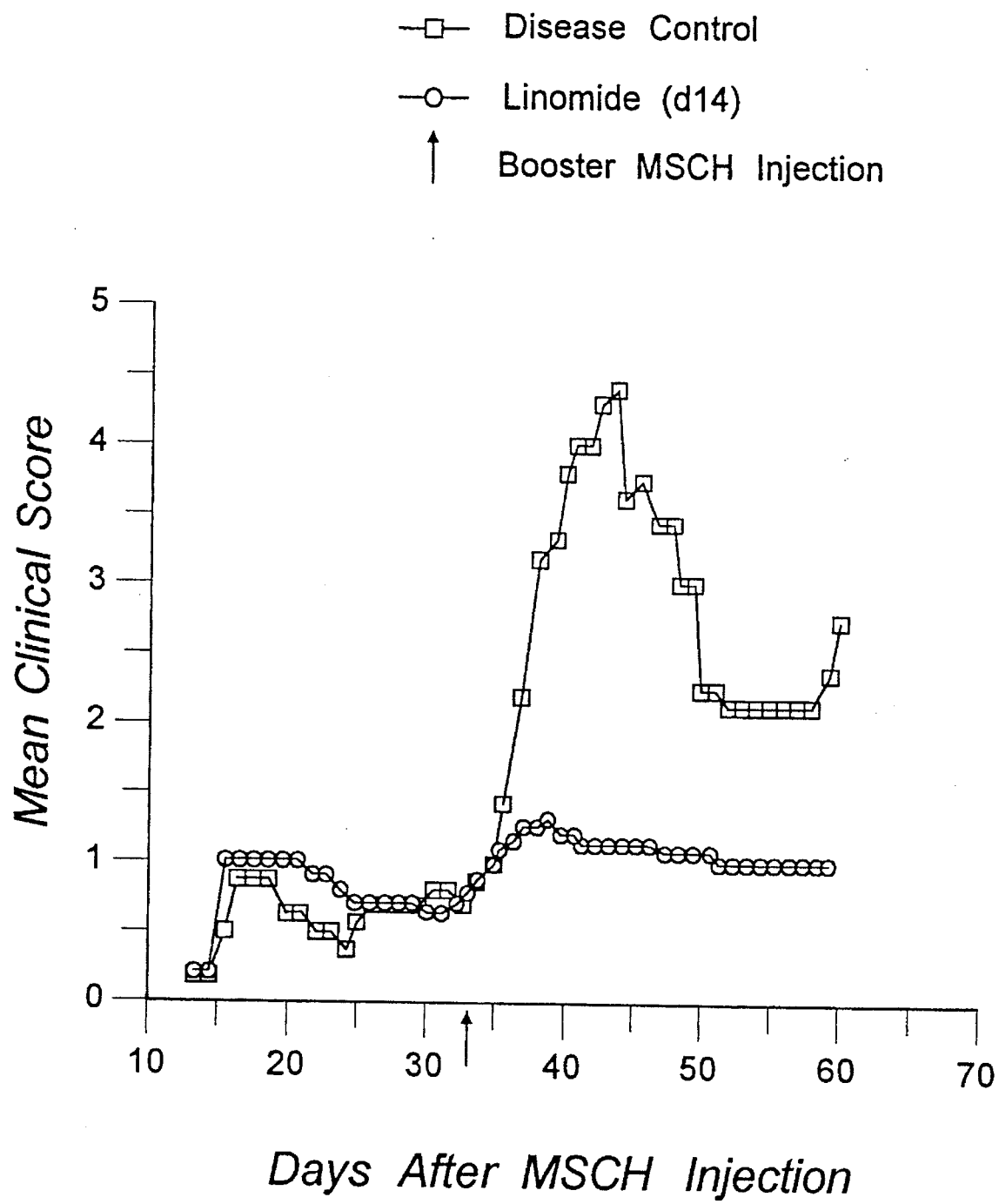
FIG. 2 is a graph showing mean clinical score of signs of chronic-relapsing experimental autoimmune encephalo-myelitis (CR-EAE) as a function of time after induction of disease in animals by injection of mouse spinal cord homogenate (MSCH). Squares represent untreated, diseased controls. Circles represent diseased animals treated daily with linomide (d7), beginning on day 14 post MSCH injection.

Linomide did not significally affect the course of CR-EAE during a short-term observation period when it was given after the onset of clinical signs (FIG. 2). Nevertheless, Linomide treated mice proved resistant to a booster injection of MSCH; only 2/8 mice developed a relapse (mild) whereas 8/8 of untreated animals had a severe relapse with 65% mortality (table 2, FIG. 2).

3. Pathologic examination

A large number of infiltrating lesions into the white matter of brain and spinal cord (perivascular and periventricular) as well as demyelinating areas around the ventricles and in cerebellum white matter, were prominent in sections of all of the untreated mice.

Clinically healthy, Linomide treated mice did not feature any CNS pathology; infiltrating or demyelinating lesions were not found in all brain and spinal cord sections investigated. Typical histological findings in untreated controls included large demyelinating areas in the white matter of the brain and the spinal cord including a large number of infiltrating lesions.

Our results show that Linomide can prevent the onset and markedly ameliorate an incipient paralytic attack, even when administrated after the onset of the disease (16–19). Successfully treated mice with no clinical evidence of disease showed no evidence of pathological signs of CR-EAE, even after the exposure to a booster injection of MSCH that produced a severe attack in all untreated animals.

TABLE 1

| Linomide administration on day 7 | | |
|---|---|---|
| | untreated controls | linomide treated |
| incidence of paralysis | 19/20 | 0/16 |
| incidence of relapse after MSCH injection | 10/10 | 2/8 |
| mortality | 6/10 | 0/8 |

TABLE 2

| Linomide administration on day 14 | | |
|---|---|---|
| | untreated controls | linomide treated |
| incidence of paralysis | 6/8 | 4/8 |
| incidence of relapse after MSCH injection | 8/8 | 2/8 |
| mortality | 5/8 | 0/8 |

References

1. Prineas, J. W.: The neuropathology of multiple sclerosis. In: Koetsier, J. C. (ed.) Handbook of Clinical Neurology, pp. 213–257. Elsevier Science Publ., Amsterdam, 1985.

2. Oksenberg, J. R., Stuart, S., Begivich, A. B., Bell, R. B., Erlich, H. A., Steinman, L. and Bernard, C.A.: Limited heterogeneity of rearranged T-cell receptor Va transcripts in brains of multiple sclerosis patients. Nature 345:344–347, 1990.

3. Myrianthopoulos, N. C.: Genetic aspects of multiple sclerosis. In: Koetsier, J. C. (ed.) Handbook of Clinical Neurology, pp 289–317. Elsevier Science Publ., Amsterdam, 1985.

4. Mehta, P. J., Miller, J. A. and Tourtelotte, W. W.: Oligoclonal IgG bands in plaques from multiple sclerosis brains. Neurol. 32:372–77, 1982.

5. Dhib-Jalbut, S. and McFarlin, D. E.: Immunology of multiple sclerosis. Annal. Allergy 64:433–444, 1990.

6. Hauser, S. L., Dawson, D. M. and Lehrich, J. R.: Intensive immunosuppression in multiple sclerosis. N. Eng. J. Med. 308:173–183, 1983.

7. Cook, S. D., Devereux, C., Troiano, R., Zito, G., Hafstein, M., Lavenhar, M., Hernandez, E. and Dowling, P. C.: Total lymphoid irradiation in multiple sclerosis: blood lymphocytes and clinical course. Ann. Neurol. 22:634–638, 1987.

8. Patzold, U., Hecker, H., Pocklington, P.: Azathioprine in the treatment of multiple sclerosis: final results in a 4½ year controlled study of its effectiveness covering 115 patients, J. Neurolog. Sci. 54:377–394, 1982.

9. Kappos, L., Patzold, U., Dommasch, D., Poser, S., Haas, J., Krauseneck, P., Malin, J. -P., Frierz, W., Graffenried, B. U. and Gugerli, U.S.: Cyclosporine versus axathioprine in the long-term treatment of multiple sclerosis—Results of the German multicenter study. Ann. Neurol. 23:56–63, 1988.

10. Larsson, E. L, Joiki, A. L and Stålhandske, T.: Mechanism of action of the new immunomodulator LS 2616, Int. J. Immunopharmacol. 9:425, 1987.

11. Carlsten, H., Tarkowski, A., and Nilsson, L-Å: The effect of immunomodulating treatment on cutaneous delayed hypersensitivity in MRL (1 pr/1 pr) mice, APMIS 97:728, 1989.

12. Kalland, T., Alm, G., and Stålhandske, T.: Augmentation of mouse natural killer cell activity by LS 2616, a new immunomodulator, J. Immunol. 134:3956, 1985.

13. Kalland, T.: Regulation of NK progenitors: Studies with a novel immunmodulator with distinct effects at the precursor level, J. Immunol. 144:4472–6, 1990.

14. Kalland, T.: Effects of the immunomodulator LS 2616 on growth and metastatis of the murinne B16-F10 melanoma. Cancer Res. 46:3018, 1986.

15. Tarkowski, A., Gunnarsson. K., Nilsson, L-Å, Lindholm, L., and Stålhandske, T.: Successful treatment of autoimmunity in MRL/1 pr mice with LS2626, a new immunomodulator. Arthr. Rheum. 29:1405–1409, 1986.

16. Karussis DM., Vourka-Karussis U., Mizrach-Koll R., Lehmann D., Slavin S., Abramsky O.: Successful treatment of chronic-relapsing experimental autoimmune encephalomyelitis with Lindome. J Neuroimmunol. 1991;1 (suppl): 159.

17. Karussis DM., Slavin S., Vourka-Karussis U., Mizrachi-Koll R., Lehmann D., Abramsky O.: Treatment of SJL/J mice with Linomide (LS-2616) inhibits the onset and prevent relapses of chronic-relapsing experimental automimmune encephalomyelitis (CR-EAE). Neurology 42 (suppl 3): 346.

18. Karussis DM., Slavin S., Vourka-Karussis U., Mizrachi-Koll R., Lehmann D., Kalland T., Abramsky O.: Successful treatment of murine and rat experimental autoimmune encephalomyelitis (EAE) with Linomide (LS-2616), a novel immunomodulator. Autoimmunity 1992: 101.

19. Karussis DM., Slavin S., Vourka-Karussis U., Mizrachi-Koll R., Lehmann D., Abramsky O.: Successful treatment of murine and rat experimental autoimmune encephalomyelitis (EAE) with Linomide (LS-2616). J Neurol 1992;239 (suppl 2):S96.

We claim:

1. A method for treating a patient suffering from multiple sclerosis, comprising administering to the patient an effective therapeutic dose of N-phenyl-N-methyl-1,2-dihydro-4-hydroxy-1-methyl-2-oxo-quinoline-3-carboxamide, or a pharmaceutically acceptable salt of said compound.

2. A method for treating a patient suffering from multiple sclerosis, comprising administering to the patient an effective therapeutic dose of N-phenyl-N-methyl-1,2-dihydro-4-hydroxy-1-methyl-2-oxo-quinoline-3-carboxamide or tautomers thereof, or a pharmaceutically acceptable salt of said compound or tautomers thereof.

* * * * *